United States Patent [19]

Atsumi et al.

[11] 4,140,788

[45] Feb. 20, 1979

[54] N-SUBSTITUTED IMIDAZOLECARBOXAMIDE DERIVATIVES

[75] Inventors: Toshio Atsumi, Ashiya; Yuzo Tarumi, Nishinomiya; Norboru Yoshida, Osaka, all of Japan

[73] Assignee: Sumitomo Chemical Company, Limited, Japan

[21] Appl. No.: 849,515

[22] Filed: Nov. 7, 1977

[30] Foreign Application Priority Data

Nov. 10, 1976 [JP] Japan .................... 51-135681
Jul. 29, 1977 [JP] Japan .................... 52-92118

[51] Int. Cl.$^2$ .................... A61K 31/415; C07D 233/64
[52] U.S. Cl. .................... 424/273 R; 548/301; 548/337
[58] Field of Search .................... 548/301, 337; 424/273 R

[56] References Cited

PUBLICATIONS

Mizuno et al. Jour. of Antibiotics 1974, vol. 27, pp. 775-782.
Noller Chemistry of Organic Compounds end ed., pp. 244-245, Philadelphia, Saunders, 1957.
Schipper et al., Jour. Amer. Chem. Soc. 1952, vol. 74, pp. 350-353.
Sakaguchi et al., Jour. of Antibiotics 1975, vol. 28, pp. 798-803.
Tsujino et al., Proceedings of the First Intersectional Congress of IAMS 1974, vol. 3, pp. 441-443.
Saito Oyo-yakuri 1970, vol. 4, pp. 521-524.
Cunningham et al. Immunology 1968, vol. 14, pp. 599-600 & the page facing p. 600.
Miller et al., Jour. Amer. Chem. Soc. 1952, vol. 74, pp. 2892-2893.
Sakaguchi et al., Cancer Research 1975, vol. 35, pp. 1643-1648.
Sakaguchi et al., Proceedings of the First Intersectional Congress of IAMS 1974, vol. 3, pp. 539-541.

*Primary Examiner*—Alan L. Rotman
*Attorney, Agent, or Firm*—Wenderoth, Lind & Ponack

[57] ABSTRACT

N-Substituted imidazolecarboxamide compounds represented by the formula;

$$R_2HN-C(=O)-C(=C(OR_3))-N(R_1)-CH=N \quad (I)$$

wherein $R_1$ is hydrogen atom, lower alkyl, lower alkenyl, aralkyl, $R_2$ is hydrogen atom, lower alkyl, lower alkenyl, aralkyl, 1-adamantyl, $R_3$ is hydrogen atom, lower alkyl, aralkyl; with the proviso that one of $R_1$, $R_2$ or $R_3$ is not hydrogen when the other two are hydrogen, are produced by reacting aminomalonamide derivative with orthoformate derivative in high yields. The compounds (I) exhibit anti-tumor activity against experimental tumors such as Sarcoma 180 in mice.

12 Claims, No Drawings

N-SUBSTITUTED IMIDAZOLECARBOXAMIDE DERIVATIVES

The present invention relates to novel imidazole-carboxamide derivatives and preparation thereof. More particularly, the present invention pertains to N-substituted imidazole-4-carboxamide derivatives useful as anti-cancer agents, and to their preparation and use.

So far, it is known that Bredinin, 4-carbamoyl-1-$\beta$-D-ribofuranosylimidazolium-5-olate, has immunosuppressive activity and weak antitumor activity against lymphatic leukemia L 1210. [Kimio Mizuno et al. J. of Antibiotics, 27, 775 (1974)].

The aglycone of Bredinin, 4-carbamoylimidazolium-5-olate, is also known. [Edgar Shipper et al. J. Amer. Chem. Soc., 74, 350 (1952)]. However, the biological properties of 4-carbamoylimidazolium-5-olate were not known till quite recently.

It is reported that growth inhibitory effects on L-5178Y cells and immunosuppressive effects are produced by administration of 4-carbamoylimidazolium-5-olate [Kenzo Sakaguchi et al. J. of Antibiotics, 28, 798 (1975), T. Tsujino et al. Proceedings of the First Intersectional Congress of IAMS vol. 3, 441 (1974)].

One of the present inventors and co-workers found that 4-carbamoylimidazolium-5-olate possesses strong anticancer activity against Sarcoma 180 (Japanese Patent Application No. 107520/76).

N-Substituted 4-carbamoylimidazolium-5-olate derivatives provided by the present invention are representable by the formula:

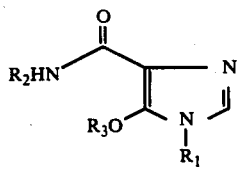

wherein $R_1$ is hydrogen, lower alkyl, lower alkenyl, aralkyl, $R_2$ is hydrogen, lower alkyl, lower alkenyl, aralkyl, 1-adamantyl, $R_3$ is hydrogen, lower alkyl, aralkyl, with the proviso that one of $R_1$, $R_2$ or $R_3$ is not hydrogen atom when the other two are hydrogen.

As used herein, the term "lower alkyl" may preferably include a straight or branched alkyl having 1 to 3 carbon atoms (e.g. methyl, ethyl, n-propyl, isopropyl). The term "lower alkenyl" may preferably include alkenyl having 3 to 5 carbon atoms (e.g. allyl, methallyl, 2-butenyl, 3,3-dimethylallyl). The term "aralkyl" may preferably include unsubstituted or $C_1$-$C_3$ alkoxy substituted benzyl.

According to the present invention, N-substituted imidazolecarboxamide derivatives of the formula:

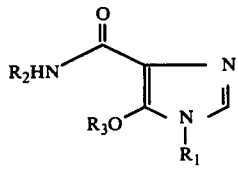

wherein $R_1$, $R_2$ and $R_3$ are as defined above, can be prepared by reacting $\alpha$-alkoxycarbonylglycine derivative of the formula:

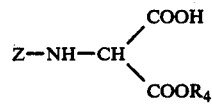

wherein $R_4$ is lower alkyl, Z is benzyloxycarbonyl, with amine having the formula:

wherein $R_5$ is lower alkyl, aralkyl, 1-adamantyl, to give $\alpha$-alkoxycarbonylglycineamide derivative of the formula:

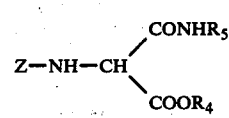

wherein $R_4$, $R_5$ and Z are as defined above, reacting the resultant $\alpha$-alkoxycarbonylglycineamide derivative with ammonia to give N-benzyloxycarbonylaminomalonamide derivative of the formula:

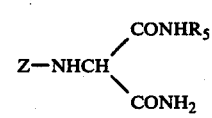

wherein $R_5$ and Z are as defined above, eliminating the benzyloxy carbonyl group from the resultant N-benzyloxycarbonylaminomalonamide derivative by the catalytic hydrogenation to give aminomalonamide derivative of the formula:

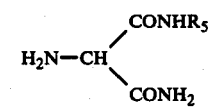

wherein $R_5$ is as defined above, or reacting aminomalonate derivative of the formula:

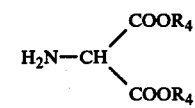

wherein $R_4$ is as defined above or its salt, with amine having the formula:

wherein $R_6$ is lower alkyl, lower alkenyl, aralkyl, to give aminomalonamide derivative of the formula:

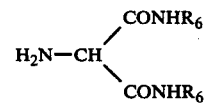

wherein $R_6$ is as defined above, and reacting the resultant aminomalonamide derivative (VI) or (IX) with orthoformate of the formula:

wherein $R_4$ is as defined above.

Among the preferred compounds are those wherein $R_1$ is lower alkyl, benzyl or $C_1$-$C_3$ alkoxy-substituted benzyl, $R_2$ is hydrogen, $R_3$ is hydrogen, lower alkyl, benzyl or $C_1$-$C_3$ alkoxy substituted benzyl or $R_1$ is hydrogen, $R_2$ is lower alkyl, benzyl, $C_1$-$C_3$ alkoxy-substituted benzyl or 1-adamantyl, $R_3$ is hydrogen or wherein $R_1$ and $R_2$ are lower alkyl, lower alkenyl, benzyl or $C_1$-$C_3$ alkoxy-substituted benzyl, $R_3$ hydrogen, lower alkyl, benzyl or $C_1$-$C_3$ alkoxy-substituted benzyl.

The process of the present invention is explained in due order as follows.

Firstly, the process for producing α-alkoxycarbonylglycineamide derivative (IV) by condensing (II) and (III) will be described. This condensation reaction can be carried out by the usual method of peptide synthesis, for example, by the method of dicyclohexylcarbodiimide (DCC) method, DCC-N-hydroxysuccinimide method, DCC-1-hydroxybenzotriazole method, etc., and mixed anhydrides using ethyl chloroformate, isobutyl chloroformate, etc. As the solvent, for example, such organic solvents as tetrahydrofuran, dioxane, chloroform, dichloromethane, benzene, toluene, etc. are used.

It is preferable to carry out this condensation reaction in tetrahydrofuran under cooling by the method of DCC-N-hydroxybenzotriazole.

Next, N-benzyloxycarbonylaminomalonamide derivative (V) can be obtained by reacting α-alkoxycarbonylglycineamide derivative (IV) with ammonia in lower alcohol. Within a range of temperature from 0° to 40° C., the reaction generally proceeds but temperature ranging from 0° to 5° C. is preferable. N-benzyloxycarbonylaminomalonamide derivative (V) is dissolved in an adequate solvent, for example, methyl alcohol or ethyl alcohol. Then catalytic hydrogenation can be carried out in the presence of catalyst, for example, palladium black, palladium-carbon, palladium-barium carbonate, platinum, but preferably palladium-calcium carbonate can be used in order to prevent the side reaction. The aimed aminomalonamide derivative (VI) is easily obtained as crystals.

The another aminomalonamide derivative (IX) can be obtained by heating the mixture of aminomalonate derivative (VII) or its salts and amine derivative (VIII). The reaction can proceed more easily under sealed reaction vessel. Lastly the process for producing N-substituted imidazole-carboxamide (I) by the reaction of aminomalonamide derivative (VI) or (IX) with orthoformate (X) will be described. This reaction proceeds smoothly without a solvent but it is preferable to use a suitable solvent in many cases. As the solvent, for example, such non-polar organic solvents as toluene, benzene, dichloromethane, chloroform, etc. and other organic solvents, such as tetrahydrofuran, dioxane, methyl alcohol and ethyl alcohol are used. Among them, lower alcohol is most suitable. The reaction temperature ranging from 50° to 100° C. is preferable. This reaction is carried out in the presence of catalyst in some cases, for example, such organic acid as acetic acid or such mineral acid as hydrochloric acid.

If desired, imidazole derivative (I) is obtained by alkylating the derivative (I, $R_3$ = H) with dialkyl sulfate, alkyl halide, diazoalkane, aralkyl halide, etc. This reaction is carried out in water or organic solvents in the presence of organic base or inorganic base. In the process of imidazole cyclization of aminomalonamide derivative (VI), two kind of products (A) and (B) are obtained.

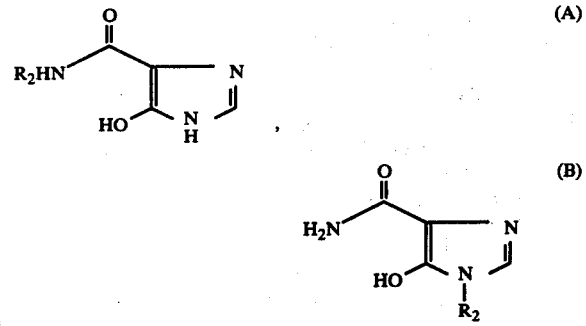

(B) Derivative is the major product, but when $R_2$ is 1-adamantyl, the amount of (B) is negligible. The separation of (A) and (B) is carried out easily with recrystallization of them from lower alcohol, for example, methyl alcohol, ethyl alcohol or isopropyl alcohol, etc.

The present inventors found out that N-substituted imidazolecarboxamide derivatives (I) possess potent anti-cancer activity against experimental mouse tumors such as Sarcoma 180. The derivatives (I) of the present invention have low toxicity. They do not show any toxic symptoms, when over 500 mg/kg of the compounds are orally administerted to a mouse. Moreover, they do not show immunosuppressive activity, which is one of the most serious side effects of anticancer agents.

In the following, the anticancer and the immunosuppressive activities of the compounds (I) are described. The anticancer activities were estimated according to the methods described in "Oyo-yakuri" vol. 4, p. 521 (in Japanese). The immunosuppressive activities were estimated according to the methods described in "Immunology" vol. 14, p. 599 (1968).

The results are described in Table.

| Compounds (I) | Anticancer effects on mouse experimental tumors | | | Immunosuppressive effects on mouse | |
|---|---|---|---|---|---|
| | Dosage mg/kg day | Route | Inhibition ratio (%) Sarcoma (solid) | Dosage mg/kg/ day (p.o.) | Suppression (%) |
| A ($R_1$= $CH_2Ph$, $R_2$=$R_3$=H) | 170 × 5 | i.p. | 32.8 | 25 × 4 | 9.7 |
| B ($R_1$= $CH_3$, $R_2$=$R_3$=H) | 111 × 5 | i.p. | 45.3 | 14 × 4 | 10.6 |
| C ($R_1$=P—$CH_3O$—$C_6H_4CH_2$, $R_2$=$R_3$=H) | 200 × 5 | i.p. | 29.1 | 25 × 4 | 10 |
| D ($R_1$=H, $R_2$=P—$CH_3O$—$C_6H_4CH_2$, $R_3$=H) | 200 × 5 | i.p. | 26.5 | — | — |
| E ($R_1$=$R_2$=$CH_3$, | 122 × 5 | i.p. | 39.1 | 200 × 4* | 1.8 |

| Compounds (I) | Anticancer effects on mouse experimental tumors | | | Immunosuppressive effects on mouse | |
|---|---|---|---|---|---|
| | Dosage mg/kg day | Route | Inhibition ratio (%) Sarcoma (solid) | Dosage mg/kg/ day (p.o.) | Suppression (%) |
| F ($R_1=R_2=PhCH_2$, $R_3=H$) | 200 × 7 | p.O. | 36.5 | 200 × 4 | 4.3** |
| G ($R_1=R_2=R_3=CH_3$) | 134 × 5 | i.p. | 32.2 | — | — |
| H ($R_1=H$, $R_2=1—$adamantyl, $R_3=H$) | 206 × 5 | i.p. | 44.1 | — | — |
| 4-carbamoyl-imidazolium-5-olate | 100 × 7 | i.p. | 50.3 | 12.5 × 4 | 61.1 |

*s.c. administration
**immunostimulation

Thus, the compounds of the present invention are useful against tumors in mice. The compounds of the present invention can be administered orally or parenterally at a daily dose in a conventional dosage unit form. For the oral or parenteral administration, they are made up alone or together with a conventional pharmaceutical carrier or diluent to a conventional solid or liquid pharmaceutical preparation (e.g. powders, granules, tablets, capsules, suspension, emulsions, solutions) using the conventional methods of pharmaceutical field.

The following examples are given to illustrate the present invention more precisely but they are not intended to limit the present invention thereto.

EXAMPLE 1

To a solution of 40 ml of 95% ethyl alcohol containing 12.69 g of ethyl aminomalonate hydrochloride was added 45 ml of 30% methylamine ethyl alcohol solution. The mixture was heated at 60° C. for 5 hours in the sealed tube. After evaporating off the solvent under reduced pressure, 40 ml of chloroform was added to the resultant residue. The separated methylamine hydrochloride was filtered off, the filtrate was concentrated to give the crystals (8.8 g). Thus obtained aminomalondimethylamide (IX) ($R_6 = CH_3$) 8.8 g was dissolved in 30 ml of dry ethyl alcohol. To this solution were added 44.4 g of ethyl orthoformate and 0.5 ml of acetic acid, and the mixture was refluxed for 30 minutes. After cooling, the separated crystals were collected by filtration to give the crude 1-methyl-5-hydroxy-1H-imidazole-4-(N-methyl)-carboxamide. Recrystallization from the solution of 99% ethyl alcohol and isopropylether gave 6.61 g of pure product. (Yield 71%) m.p. 226.5°-227° C.

EXAMPLE 2

To the solution of 930 mg of 1,-methyl-5-hydroxy-1H-imidazole-4-(N-methyl)-carboxamide in 100 ml of dry ethyl alcohol was added the ethyl ether solution of diazomethane under cooling till the evolution of nitrogen gas ceased. After 10 minutes, the reaction was completed, the reaction mixture was condensed under reduced pressure to give the crystals. Recrystallization from the solution of chloroform, isopropyl ether and n-hexane gave 895 mg of pure 1-methyl-5-methoxy-1H-imidazole-4-(N-methyl). (Yield 88%) m.p. 113°-116° C.

EXAMPLE 3

The mixture of 2.33 g of 1-methyl-5-hydroxy-1H-imidazole-4-(N-methyl)-carboxamide, 2.10 g of potassium carbonate, 9.37 g of methyliodide, 10 ml of dry dimethylformamide and 80 ml of dry acetone was heated at 70° C. for one hour. After the reaction was complete, the reaction mixture was condensed under reduced pressure and chloroform was added to the residue and the insoluble materials were filtered off. The filtrate was concentrated to give the crude, 1-methyl-5-methoxy-1H-imidazole-4-(N-methyl)-carboxamide. Recrystallization from the same solvent as described in Example 2 to give 2.5 g of pure compound. m.p. 113°-116° C. The following compounds were obtained by substantially the same procedures as described above.

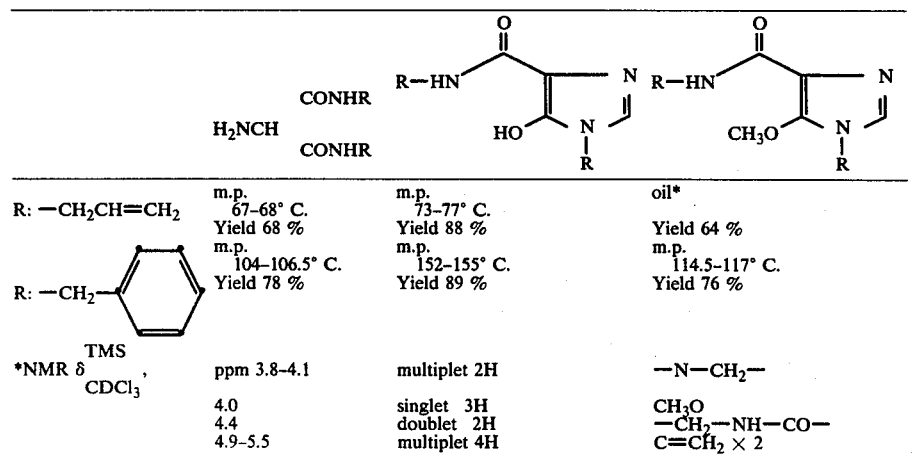

-continued

| | | |
|---|---|---|
| H$_2$NCH‹CONHR, CONHR | (structure: R—HN-C(=O)-C=C(OH)-N=CH-N(R) ring) | (structure: R—HN-C(=O)-C=C(OCH$_3$)-N=CH-N(R) ring) |
| 5.6–6.2 | multiplet 2H | CH=C × 2 |
| 7.4 | singlet 1H | C$_2$—H |

EXAMPLE 4

To the mixture of 2.81 g of N$^\alpha$-benzyloxycarbonyl-α-ethoxycarbonylglycine, 1.0 g of 30% methylamine ethyl alcohol solution, 1.48 g of 1-hydroxybenzotriazole and 25 ml of dry tetrahydrofuran was added dropwisely 2.06 g of dicyclohexylcarbodiimide in 15 ml of dry tetrahydrofuran at −7° C. under cooling and allowed to react with stirring for 19 hours at room temperature. Then the separated dicyclohexylurea was filtered off and the filtrate was condensed under reduced pressure to give 5.02 g of oily residue, which was dissolved in ethyl acetate. The solution was washed with N-hydrochloric acid solution two times, saturated sodium chloride solution, sodium bicarbonate solution and water, dried over anhydrous sodium sulfate. The solvent was removed under reduced pressure to give 2.86 g of crude crystals. Yield 97%. Recrystallization from the solution of chloroform and isopropylether gave N$^\alpha$-benzyloxycarbonyl-α-ethoxycarbonlglycine methylamide, m.p. 123.5°–124.5° C. Thus obtained N$^\alpha$-benzyloxycarbonyl-α-ethoxycarbonylglycine methylamide 10.3 g was dissolved in 120 ml of methyl alcohol, and 16% ammonia methyl alcohol solution was added therein. The reaction vessel was sealed completely, and it was allowed to stand in the refrigerator for 44 hours. The separated crystals were collected by filtration to give 8.05 g of the desired compound, and further the filtrate was concentrated to give 1.36 g of crystals, which were recrystallized from the solution of methyl alcohol and isopropyl ether to give 0.6 g of pure N$^\alpha$-benzyloxycarbonyl-α-carbamoylglycine methylamide, m.p. 178.5°–179.5° C., Yield 93% (8.65 g).

The mixture of 5.31 g of N$^\alpha$-benzyloxycarbonyl-α-carbamoylglycine methylamide, 100 ml of dry tetrahydrofuran, and 100 ml of methyl alcohol was reduced in the presence of 1.5 g of 10% palladium-calcium carbonate under hydrogen atmosphere for 17 hours. The catalyst was filtered off, the filtrate was concentrated under reduced pressure to give 2.9 g of crystals. Recrystallization from the solution of 99% ethyl alcohol and isopropyl ether to give 2.21 g of α-carbamoylglycine methylamide, m.p. 121°–122.5° C., Yield 84.4%.

α-Carbamoyglycine methylamide 1.57 g was dissolved in 50 ml of dry ethyl alcohol, and 8.95 g of ethyl orthoformate was added to it, then the mixture was refluxed for 1.5 hours. The separated crystals were collected by filtration to give 1.302 g, Yield 76% of the mixture, 1-methyl-5-hydroxy-1H-imidazole-4-carboxamide (B) and 5-hydroxy-1H-imidazole-4-(N-methyl)-carboxamide (A). It was found that the ratio of (A)/(B) is 40/60 by NMR analysis. Recrystallization from methyl alcohol to give 417 mg of 1-methyl-5-hydroxy-1H-imidazole-4-carboxamide, m.p. 222.5° C., and 250 mg of 5-hydroxy-1H-imidazole-4-(N-methyl)-carboxamide, m.p. 237.0° C.

The following compounds were obtained by substantially the same procedures as described above.

| R | ZNHCH(CONHR)(COOEt) | ZNHCH(CONHR)(CONH₂) | H₂NCH(CONHR)(CONH₂) | RHN-C(=O)-C(=C(OH))-N=CH-N-H | H₂N-C(=O)-C(=C(OH))-N=CH-N-R |
|---|---|---|---|---|---|
| —CH₂CH₂CH₃ | m.p. 70–71° C. Yield 99.0 % | m.p. 153–154° C. Yield 93.0 % | m.p. 132.5–133.5° C. Yield 87 % | m.p. 247° C. (dec.) Yield 39.3 % | m.p. 214.5–217.5° C. Yield 58.7 % |
| —CH₂—C₆H₄—OCH₃ | m.p. 127–127.5° C. Yield 94.0 % | m.p. 168–169° C. Yield 96.0 % | m.p. 172.5–173° C. Yield 93.0 % | m.p. 243.5° C. Yield 25 % | m.p. 220° C. (dec.) Yield 50 % |
| —CH₂—C₆H₅ | m.p. 138–139.5° C. Yield 74 % | m.p. 175.5–176° C. Yield 79 % | m.p. 144–148.5° C. Yield 59 % | m.p. 215° C. Yield 24 % | m.p. 249° C. Yield 65 % |
| —CH₂—(adamantyl) | m.p. 132.5–133° C. Yield 88 % | m.p. 140–141° C. Yield 88 % | m.p. 122–123° C. Yield 76 % | m.p. 273° C. (dec.) Yield 86.4 % | — |

According to the Example 3, the following compounds were obtained.

| 1-benzyl-5-benzyloxy-1H-imidazole-4-carboxamide m.p. 208.5 – 209.5° C. | | | |
|---|---|---|---|
| 1-Benzyl-5-methoxy-1H-imidazole-4-carboxamide oil, NMR $\delta_{CDCl_3}$ ppm, | 3.9 singlet | 3H —OCH$_3$ | |
| | 4.6 singlet | 2H —CH$_2$— 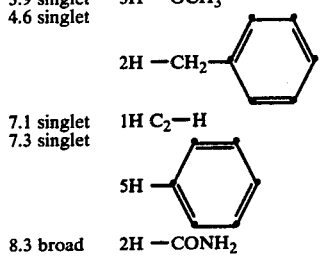 | |
| | 7.1 singlet | 1H C$_2$—H | |
| | 7.3 singlet | 5H | |
| | 8.3 broad | 2H —CONH$_2$ | |

According to the literature, for example Biochem. J. 87, 601 (1963), the starting material in this invention, N$^\alpha$-benzyloxycarbonyl-α-ethoxycarbonylglycine, was easily obtained.

What we claim is:

1. A compound of the formula,

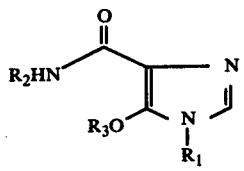

wherein R$_1$ is hydrogen, lower alkyl, lower alkenyl benzyl or C$_1$-C$_3$ alkoxy-substituted benzyl, R$_2$ is hydrogen, lower alkyl, lower alkenyl, benzyl, C$_1$-C$_3$ alkoxy substituted benzyl or 1-adamantyl, R$_3$ is hydrogen, lower alkyl, benzyl or C$_1$-C$_3$ alkoxy-substituted benzyl, with the proviso that one of R$_1$, R$_2$ or R$_3$ is not hydrogen when the other two are hydrogen.

2. A compound according to claim 1, wherein R$_1$ is lower alkyl, benzyl or C$_1$-C$_3$ alkoxy substituted benzyl, R$_2$ is hydrogen, R$_3$ is hydrogen, lower alkyl, benzyl or C$_1$-C$_3$ alkoxy substituted benzyl.

3. A compound according to claim 1, wherein R$_1$ is hydrogen, R$_2$ is lower alkyl, benzyl, C$_1$-C$_3$ alkoxy substituted benzyl or 1-adamantyl, R$_3$ is hydrogen.

4. A compound according to claim 1, wherein R$_1$ and R$_2$ are lower alkyl, lower alkenyl benzyl or C$_1$-C$_3$ alkoxy substituted benzyl, R$_3$ is hydrogen, lower alkyl, benzyl or C$_1$-C$_3$ alkoxy substituted benzyl.

5. 1-Benzyl-5-hydroxy-1H-imidazole-4-carboxamide.

6. 1-Methyl-5-hydroxy-1H-imidazole-4-carboxamide.

7. 1-(p-Methoxybenzyl)-5-hydroxy-1H-imidazole-4-carboxamide.

8. 1-methyl-5-hydroxy-1H-imidazole-4-(N-methyl)-carboxamide.

9. 1-benzyl-5-hydroxy-1H-imidazol-4-(N-benzyl)-carboxamide.

10. 1-methyl-5-methoxy-1H-imidazole-4-(N-methyl)-carboxamide.

11. 5-hydroxy-1H-imidazole-4-[N-(1-adamantyl)]-carboxamide.

12. A pharmaceutical composition, which comprises an effective amount for treating the Sarcoma 180 tumor in mice of a compound of claim 1 as an active ingredient and a pharmaceutically acceptable carrier or diluent.

* * * * *